United States Patent
Guo

(10) Patent No.: US 6,743,242 B2
(45) Date of Patent: Jun. 1, 2004

(54) DUAL-USE SUTURING DEVICE FOR SUTURING WOUND INDUCED FROM CELIOSCOPE SURGERY

(76) Inventor: Qi-Zhao Guo, 235 Chung-Ho Box 8-24, Taipei (TW)

( * ) Notice: Subject to any disclaimer, the term of this patent is extended or adjusted under 35 U.S.C. 154(b) by 173 days.

(21) Appl. No.: 10/074,435

(22) Filed: Feb. 13, 2002

(65) Prior Publication Data

US 2003/0153929 A1 Aug. 14, 2003

(51) Int. Cl.[7] ............................................. A61B 17/00
(52) U.S. Cl. ...................................... 606/148; 606/144
(58) Field of Search ............................... 606/139, 148, 606/213, 186, 187; 112/169

(56) References Cited

U.S. PATENT DOCUMENTS

| | | | | |
|---|---|---|---|---|
| 5,613,974 A | * | 3/1997 | Andreas et al. | 606/144 |
| 5,626,588 A | * | 5/1997 | Sauer et al. | 606/144 |
| 5,843,177 A | * | 12/1998 | Vanney et al. | 606/108 |
| 2002/0133129 A1 | * | 9/2002 | Arias et al. | 604/272 |
| 2003/0093093 A1 | * | 5/2003 | Modesitt et al. | 606/144 |

* cited by examiner

Primary Examiner—Michael J. Milano
Assistant Examiner—Bradford C Pantuck

(57) ABSTRACT

A dual-use suturing device for suturing a wound induced from a celioscope surgery is formed by a needle positioning seat, an auxiliary positioning device, and an upper cover buckled to the needle positioning seat. The positioning pieces at the top of the auxiliary positioning device are buckled to the embedding groove at a lower end of the needle positioning seat. The guide holes of the needle positioning seat have a tapered inner surface. Hollowed portions of the guide trenches provide clamping spaces at two sides of the auxiliary positioning device. Then two clean auxiliary positioning devices are used to clamp the wire needle and hooked needle so that the hand of the doctor can pinch the needles. The non-hollowed portions at the upper side of the guide trenches of the auxiliary positioning device are exactly formed as resisting portions for resisting against the needles.

4 Claims, 4 Drawing Sheets

FIG1-A

DUAL-USE SUTURING DEVICE FOR SUTURING WOUND INDUCED FROM CELIOSCOPE SURGERY

FIELD OF THE INVENTION

The present invention relates to surgical devices, and particularly to dual-use suturing device for suturing a wound induced from a celioscope surgery.

BACKGROUND OF THE INVENTION

The celioscope surgery discussed in present invention is a surgery which forms three small openings on the belly of a patient for placing a celioscope and a surgical knife. In that, another end of the celioscope is connected to a screen for presenting the positions of the surgical knife and the interior of the patient's body. Before performing the surgery, the belly of the patient must be filled with carbon dioxide so as to form an air layer between the skin and the internal organs. After the surgery is completed, the gas must be drawn out. Then a wire needle with suturing wires attaching therein and a hooked needle are pierced into the muscle around the wound, wherein the two needles inserting into the skin are expanded at the distal end, as illustrated in FIG. 4. Therefore, the cured skin will have a smooth surface.

However, the skin of human body is formed by a layer of derma S, a layer of lower skin S1 and a layer of outer skin. The wound from the celioscope surgery is very small and the wire needle and hooked needle pierce into the skin as a form illustrated in FIG. 4 (the inclination can not be well controlled). As a doctor desires to suture a wound, the hands of the doctors must pinch the two needles. However, there is no place for the doctor to push forwards or pull backwards the needles so that the operation is difficult. If the operation is performed reluctantly, it has a possibility of 10% that carbon dioxide will generate in the belly so that hernia occurs. As a consequence, a further surgery is needed for drawing the carbon dioxide out of the body. However, this is an unnecessary operation and a danger is possibly induced.

Therefore, in the conventional celioscope surgery, the doctor adheres a medical tape on the wound so as to avoid hernia. However, this will slow the cure process and the patient will feel uneasy at the portion around the wound. The cured skin will not be smooth and sarcoma will generate around the wound so as to present an unpleasant outlook.

SUMMARY OF THE INVENTION

Accordingly, the primary object of the present invention is to provide a dual-use suturing device for suturing a wound induced from a celioscope surgery, wherein The dual-use suturing device for suturing a wound induced from a celioscope surgery is formed by a needle positioning seat, an auxiliary positioning device at a lower end of the needle positioning seat, and an upper cover buckled to the needle positioning seat, the positioning piece at the top of the auxiliary positioning device is buckled to the embedding groove at a lower end of the needle positioning seat. The guide holes of the needle positioning seat is inclined so that the needles T and P can be inserted into the periphery of a wound. Moreover, by the gaps, 12 mm and 15 mm, of the guide holes of the needle positioning seat, the auxiliary positioning device can be buckled with the embedding groove by the positioning piece thereof along a horizontal position or a vertical position. Thereby, it can be used for a larger wound (15 mm) or a small wound (12 mm).

Another object of the present invention is to provide a dual-use suturing device for suturing a wound induced from a celioscope surgery, wherein the hollowed portions of the guide trenches of the auxiliary positioning device provide clamping spaces at two sides of the auxiliary positioning device. Thereby, the wire needle and hooked needle are guided by the guide holes of the needle positioning seat and then inserts into the periphery of a wound. When it is necessary to suture the wound, the whole suture device for assisting the needles to insert into the periphery of the wound is drawn out. Then two clean auxiliary positioning devices are used to clamp the wire needle and hooked needle so that the hand of the doctor can pinch the needles. The non-hollowed portions at the upper side of the guide trenches of the auxiliary positioning device are exactly formed as resisting portions for resisting against the needles. Thereby, as the doctor sutures the wound, the needles can be pushed and resisted so as to perform the operations of moving forwards and pulls backwards. As a result, the wound can be sutured easily.

The various objects and advantages of the present invention will be more readily understood from the following detailed description when read in conjunction with the appended drawing.

BRIEF DESCRIPTION OF THE DRAWINGS

FIG. 1–A is a schematic perspective view showing the back surface of the needle positioning seat of the present invention.

DETAILED DESCRIPTION OF THE PREFERRED EMBODIMENTS

Figure 1:
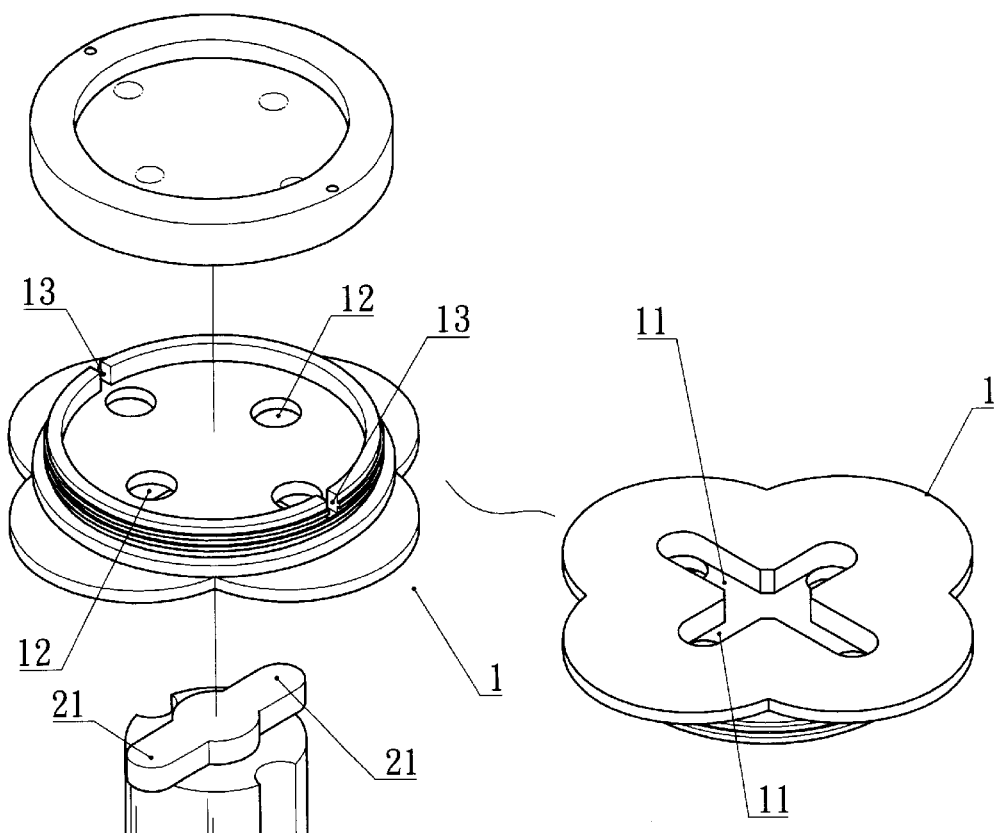
FIG. 1 is an exploded perspective view of the present invention.
Figure 1:
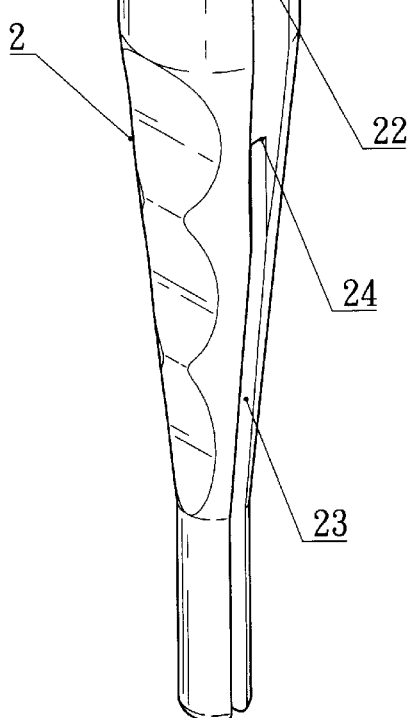
Figure 2:
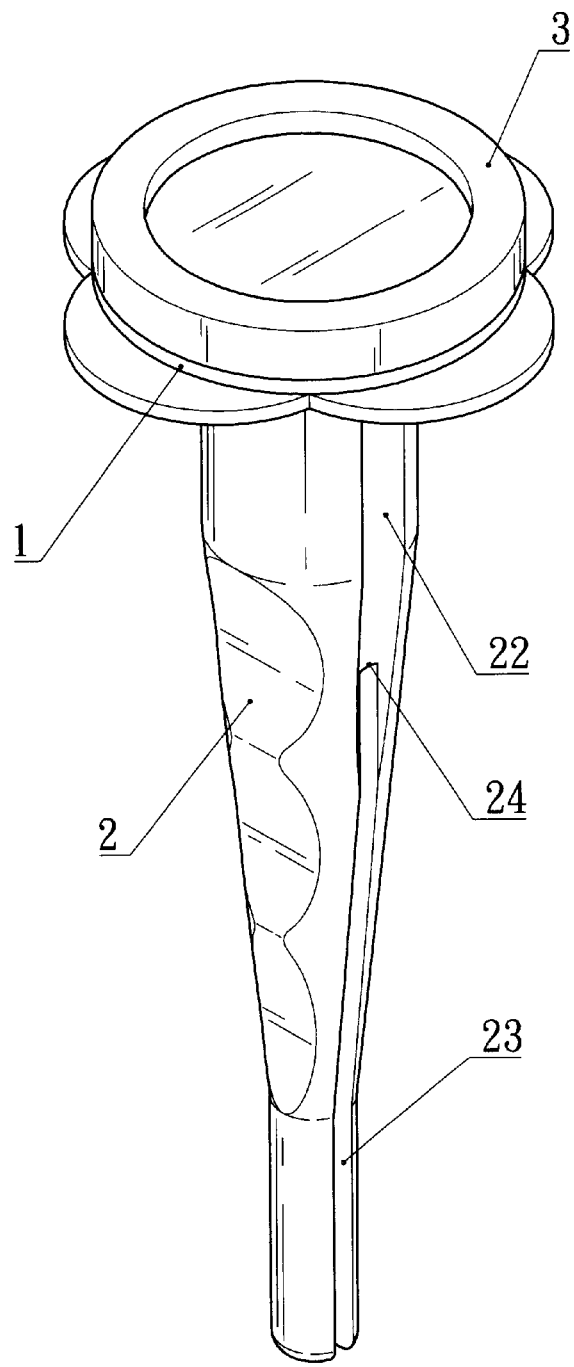
FIG. 2 is a perspective view of the present invention.

Referring to FIGS. 1 and 2, the dual-use suturing device for suturing a wound induced from a celioscope surgery of the present invention is illustrated. The dual-use suturing device for suturing a wound induced from a celioscope surgery is formed by a needle positioning seat 1, an auxiliary positioning device 2 at a lower end of the needle positioning seat 1, and an upper cover 3 buckled to the needle positioning seat 1.

A lower end of the needle positioning seat 1 has a cruciform embedding groove 11 which has four slots so as to form a cruciform structure. Each slot has a respective guide hole 12. The hole is inclined from the upper side to the lower side thereof. Therefore, a wire needle T and a hooked needle P may be guided into the hole 12. Gaps between two opposite guide holes 12 are 12 mm and 15 mm, respectively for being used in different wounds. Moreover, to match the annular edge of the auxiliary positioning device 2, the needle positioning seat 1 has tips 13 for buckling the upper cover 3.

The auxiliary positioning device 2 is a rod and two sides of the rod has a wave-like structure. A top of the auxiliary positioning device 2 has a positioning piece 21 extending from a center of the top to two sides. The positioning piece 21 can be exactly embedded into the cruciform embedding groove 11 of the needle positioning seat 1 along a horizontal or a vertical orientation so as to suit the specifications of 12 mm and 15 mm. Another two sides of the auxiliary positioning device 2 without wave-like structure are formed with guide trenches 22. Thereby, the needles T and P can be guided into the holes 12 along the trenches 22. A lower side of each guide slot 22 is formed as a clamping space 23. The clamping space 23 can be used to clamp the needles T and P so that the user's hands can pinch the needles to move upwards and downwards or leftwards and rightwards.

The upper cover 3 has a soft cover. A portion of the upper cover 3 aligned to the guide holes 12 of the needle positioning seat 1 has indicating points 31. Thereby, needles may pass through the soft upper cover 3 from the indicating points and then enter into the guide holes 12 of the needle positioning seat 1. Thereby, the upper cover 3 is installed with buckling grooves 32 at positions corresponding to the tips 13 of the needle positioning seat 1, thereby, the upper cover 3 being coupled to the upper side of the needle positioning seat 1.

Figure 3:
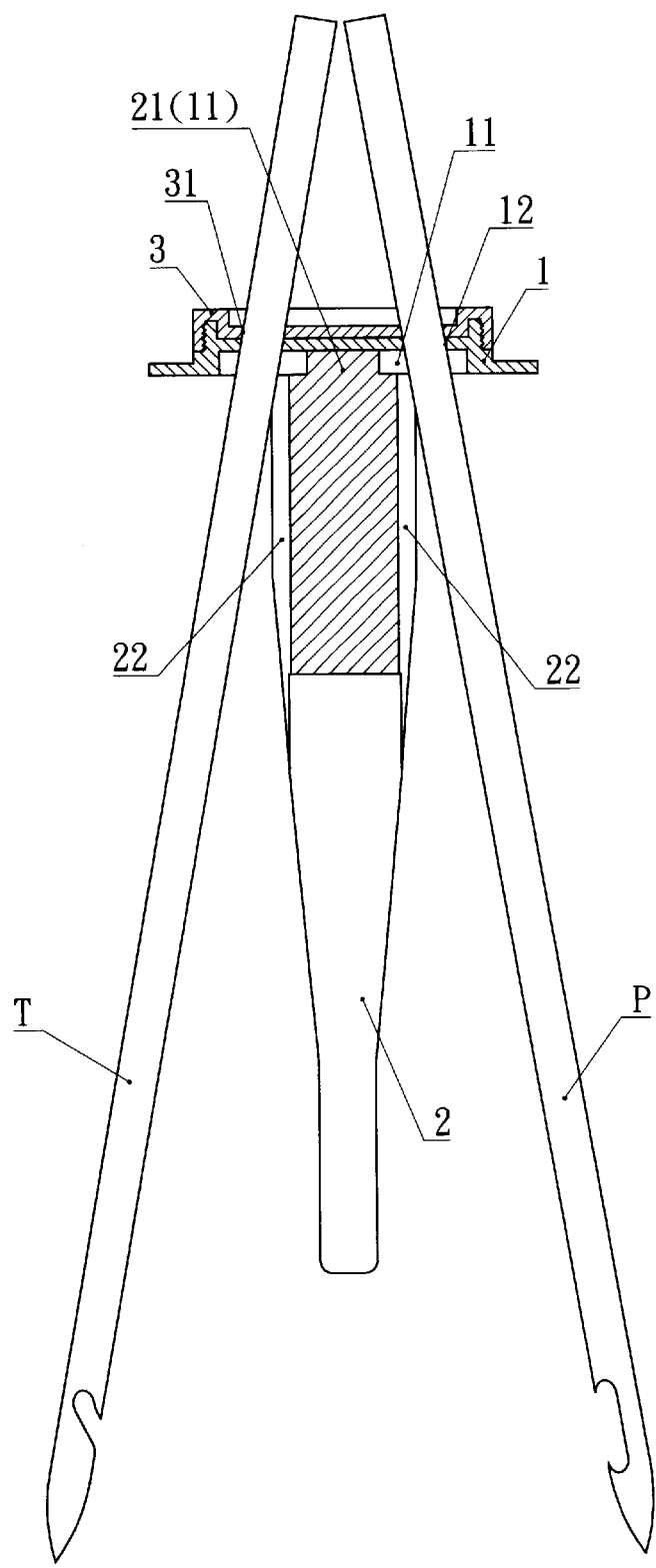
FIG. 3 is a plane assembled cross sectional view of the present invention.

The operation of the present invention will be described in the following. With reference to FIG. 3, the positioning pieces 21 at the top of the auxiliary positioning device 2 are buckled to the embedding groove 11 at a lower end of the needle positioning seat 1. The guide holes 12 of the needle positioning seat 1 is inclined so that the needles T and P can be inserted into the periphery of a wound. Moreover, by the gaps, 12 mm and 15 mm, of the guide holes 12 of the needle positioning seat 1, the auxiliary positioning device 2 can be buckled with the embedding groove 11 by the positioning piece 21 thereof along a horizontal position or a vertical position. Thereby, it can be used for a larger wound (15 mm) or a small wound (12 mm).

Figure 4:
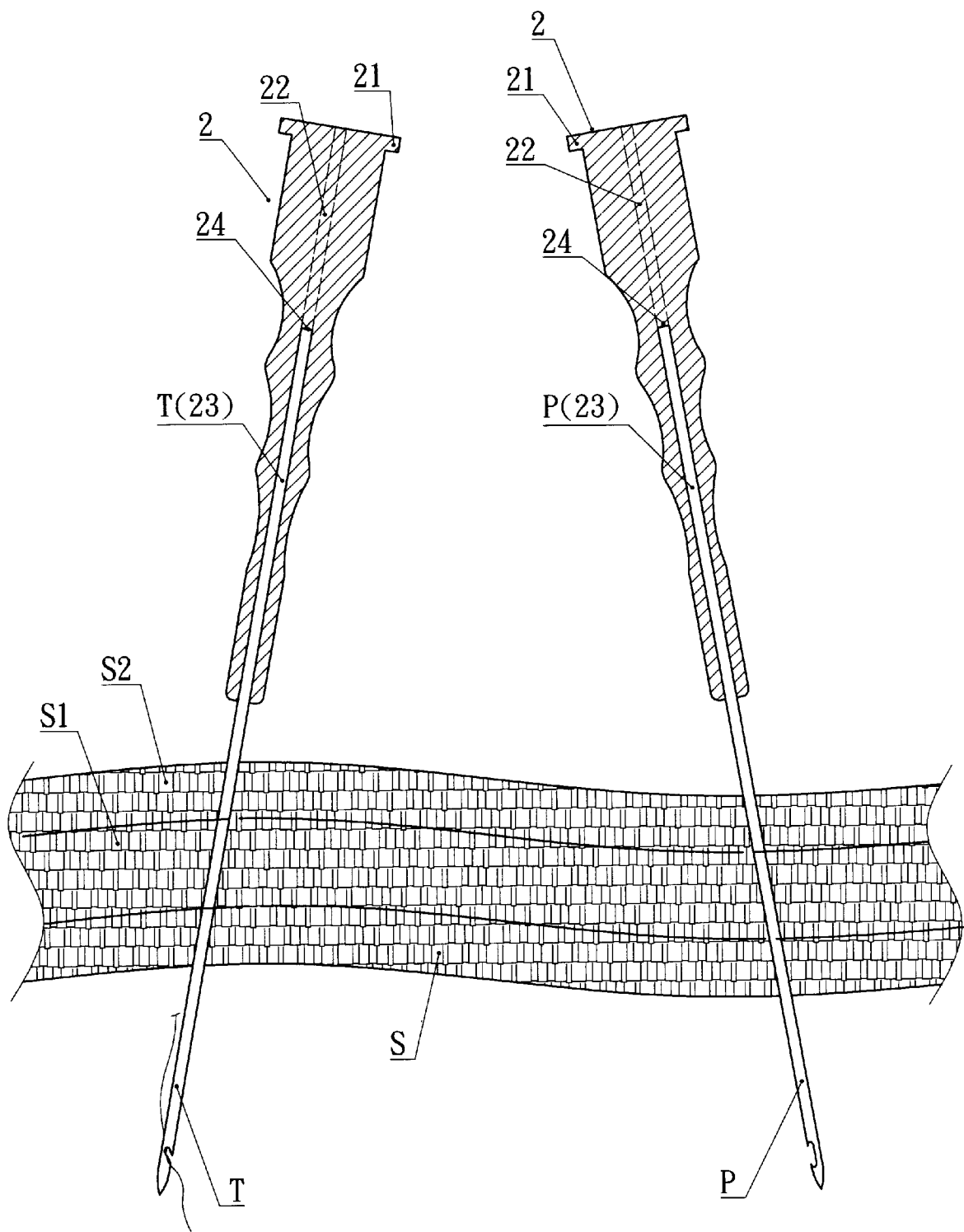
FIG. 4 shows one embodiment about the application of the auxiliary positioning device of the present invention.

With reference to FIG. 4, the hollowed portions of the guide trenches 22 of the auxiliary positioning device 2 provide clamping spaces 23 at two sides of the auxiliary positioning device 2. Thereby, when the wire needle T and hooked needle P are guided by the guide holes 12 of the needle positioning seat 1 and then insert into the periphery of a wound. When it is necessary to suture the wound, the whole suture device for assisting the needles to insert into the periphery of the wound is drawn out. Then two clean auxiliary positioning devices 2 are used to clamp the wire needle T and hooked needle P so that the hand of the doctor can pinch the needles. The non-hollowed portions at the upper side of the guide trenches 22 of the auxiliary positioning device 2 are exactly formed as resisting portions 24 for resisting against the needles. Thereby, as the doctor sutures the wound, the needles can be pushed and resisted so as to perform the operations of moving forwards and pulls backwards. As a result, the wound can be sutured easily.

Thereby, by the present invention, the wound can be sutured easily. Thereby, no carbon dioxide is accumulated in the belly and the danger of hernia is avoided.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A dual-use suturing device for suturing a wound induced from a celioscope surgery comprising:

a needle positioning seat; a lower end of the needle positioning seat having a cruciform embedding groove which has four slots; each slot having a respective guide hole; each hole has a tapered inner surface with a larger opening at a side on the slot; therefore, a wire needle and hooked needle being capable of being guided into the holes; wherein there are two pairs of holes-one having a gap of 12 mm and the other having a gap of 15 mm an auxiliary positioning device connected to a lower end of the needle positioning seat; the auxiliary positioning device having a larger end near the needle positioning seat and having a smaller end far from the needle positioning seat; a top of the auxiliary positioning device connected to the needle positioning seat having a positioning piece extending from a center of the top to two sides thereof; the positioning piece being exactly embedded into a cruciform embedding groove of the needle positioning seat along one of two orthogonal orientations; two sides of the auxiliary positioning device being formed with guide trenches; thereby, the needles are guided into the holes along the trenches; a lower side of each guide slot is hollowed and thus is formed as a clamping space; the clamping space is used to clamp the needles so that the user's hands can pinch the needles.

2. The dual-use suturing device for suturing a wound induced from a celioscope surgery as claimed in claim 1, wherein an upper side of the needle positioning seat has a soft upper cover; an edge of the needle positioning seat has tips.

3. The dual-use suturing device for suturing a wound induced from a celioscope surgery as claimed in claim 2, wherein the upper cover has indicating points at positions aligned to the guide holes of the needle positioning seat.

4. The dual-use suturing device for suturing a wound induced from a celioscope surgery as claimed in claim 1, wherein a non-hollowed portion of the guide trenches of the auxiliary positioning device is formed as a resisting portion for resisting against the needles.

* * * * *